United States Patent [19]
Jennings

[11] 4,035,168
[45] July 12, 1977

[54] NONREACTIVE INLET SPLITTER FOR GAS CHROMATOGRAPHY AND METHOD

[75] Inventor: Walter G. Jennings, Davis, Calif.

[73] Assignee: The Regents of the University of California, Berkeley, Calif.

[21] Appl. No.: 672,244

[22] Filed: Mar. 31, 1976

Related U.S. Application Data

[63] Continuation-in-part of Ser. No. 491,304, July 24, 1974, abandoned, which is a continuation-in-part of Ser. No. 421,231, Dec. 3, 1973, abandoned.

[51] Int. Cl.$^2$ .................................. B01D 15/08
[52] U.S. Cl. .............................. 55/67; 55/197; 55/386; 73/23.1; 73/422 GC
[58] Field of Search ............... 55/67, 197, 386; 73/23.1, 422 GC; 210/198 C

[56] References Cited

U.S. PATENT DOCUMENTS

| | | | |
|---|---|---|---|
| 3,327,520 | 6/1967 | Stapp, Jr. .................... | 73/23.1 |
| 3,374,660 | 3/1968 | McKinney et al. .......... | 55/386 X |
| 3,401,565 | 9/1968 | Stoll et al. .................. | 73/422 GC |
| 3,498,027 | 3/1970 | Buchtel, Sr. ................ | 55/197 |
| 3,592,046 | 7/1971 | Cramers et al. ............ | 73/23.1 |
| 3,672,226 | 6/1972 | Reid ........................... | 73/422 GC |

OTHER PUBLICATIONS

"Lectures on Gas Chromatography 1962" by Herman Szymansky, Plenum Press, New York, N. Y., 1963, pp. 24–31.
"Design Considerations and Construction of a Superior Inlet Splitter" by A. J. Ehrler, Victoreen on Chromatography, Issue No. 4 (undated), Victoreen Instrument Division.

Primary Examiner—John Adee
Attorney, Agent, or Firm—Flehr, Hohbach, Test, Albritton & Herbert

[57] ABSTRACT

An inlet splitter apparatus and method for introducing substantially unreacted linear aliquots of vaporized sample and carrier gas to the capillary column of a capillary gas chromatograph. An elongate body with separate but axially aligned injector and mixing chambers, an inert (glass) tubular liner interconnecting the separate chambers and having an inlet in the injector chamber and a baffled outlet in the mixing chamber, carrier gas injection means to introduce a stream of carrier gas through an annular passage between the elongate body and tubular liner to an inert core passage in the liner. A sample port and self-sealing septum to facilitate injection of an analysis sample to the inert liner core passage. Heating means (preheater and body heater) to vaporize the sample and pass an intermixed stream of vaporized sample and carrier gas through the inert core passage and baffled outlet of the liner. An expansion zone and metered discharge in the mixing chamber to facilitate a linear split of the sample through the inlet end of a capillary chromatograph column.

Optionally, it is preferred to increase the vaporization surface and mixing potential within the tubular liner and injection chamber by means of a packing or filler of very fine (100–120 mesh), inert material (glass beads).

The apparatus provides inert (glass) surfaces forming the pathway for the intermixed sample and carrier gas stream so that degradation of the sample by reaction with hot metallic or like surfaces is avoided. Turbulent intermixing within the baffled passageways of wholly inert (glass) components and filters assures that substantially unreacted linear aliquots of intermixed sample and carrier gas will pass to the capillary chromatograph column. The rate of flow of the carrier gas (at least 6 to 100 ml. per min.) is sufficient to insure that the apparatus is swept clean by carrier gas so that "band broadening" within the chromatograph column is avoided. Demountability of the apparatus permits removal and cleaning of the injector, liner, baffle and filter components to avoid chemical build-up and progressive sample degradation. Repetitive accuracy in capillary chromatographic analysis of very small substantially unreacted samples (e.g., 0.01 microliters) is thus assured.

40 Claims, 9 Drawing Figures

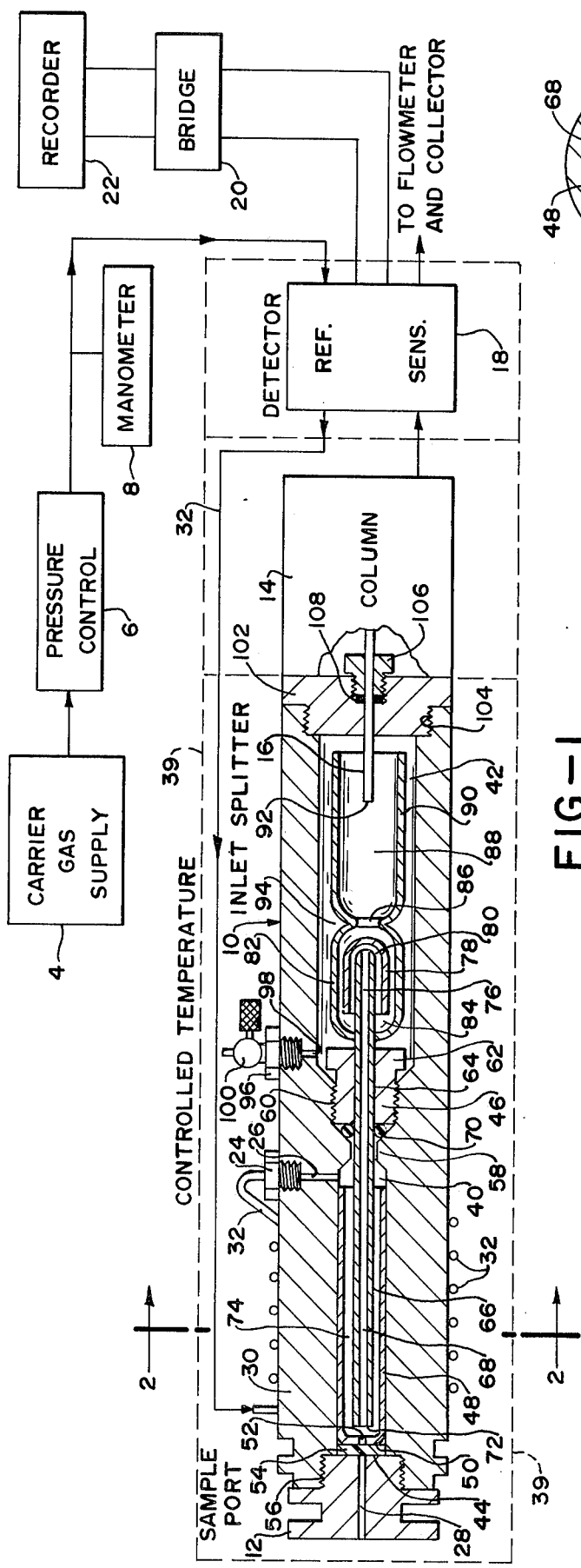
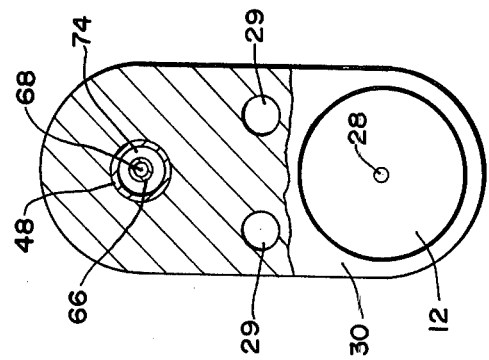
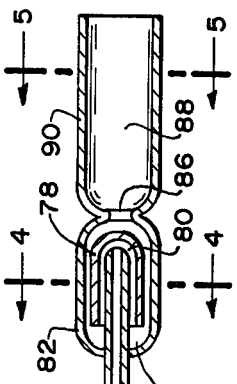
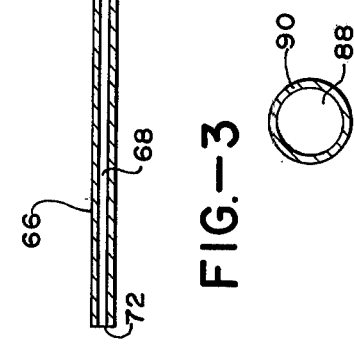
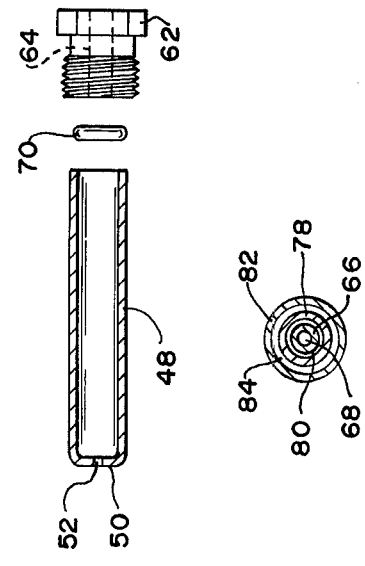

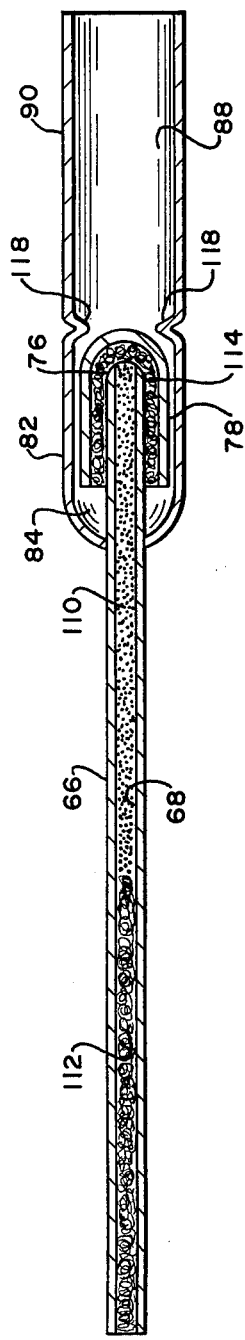
FIG.—6
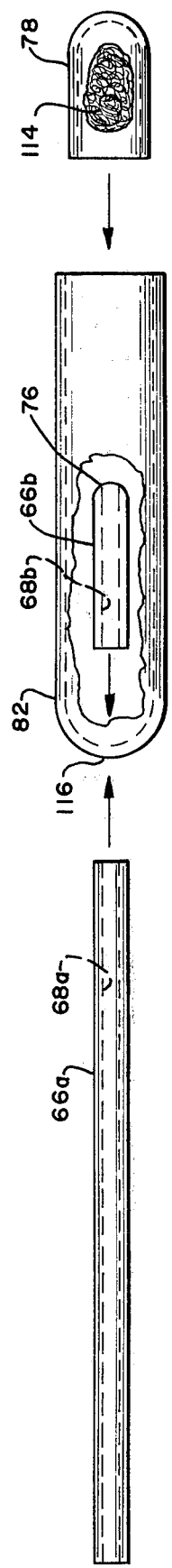
FIG.—7

NONREACTIVE INLET SPLITTER FOR GAS CHROMATOGRAPHY AND METHOD

CROSS REFERENCE TO RELATED APPLICATIONS

This application is a continuation-in-part of my co-pending application Ser. No. 491,304, filed July 24, 1974 now abandoned which, in turn, is a continuation-in-part of my application Ser. No. 421,231, filed Dec. 3, 1973, now abandoned.

BACKGROUND OF THE INVENTION

This invention relates generally to inlets for gas chromatographs and more particularly to an inlet splitter apparatus and method for a capillary gas chromatograph whereby substantially linear fractionation of intermixed sample and carrier gases is achieved to provide pure or substantially unreacted sample aliquots for chromatograph analysis.

Gas chromatography (more precisely gas-liquid chromatography) is a process by which a mixture is separated into its constituents by a moving gas phase passing over a nonvolatile liquid sorbent coated on an inert solid support. The basic apparatus comprises a column support for the sorbent, a carrier gas supply and control, a sample port or inlet, and a detector for determining the composition of the moving gas effluent from the column. In general, gas-liquid chromatographic columns are of two types: the packed column in which the liquid sorbent is distributed as a thin film on a granular support packed into the column, and the open tubular capillary column in which the interior of the capillary tube is coated with a thin layer of the liquid sorbent. The capillary columns are further classified as small-bore (i.e., about 0.25 mm) and wide-bore (i.e., about 0.75 mm). Since small-bore capillary columns can be demonstrated to give vastly superior resolution as respects the constituent components, their use is fast increasing. However, because of their small size, small-bore capillary columns present a number of problems. One of these problems is the greatly reduced sample capacity of the small-bore column, which limits sample injections to amounts of the order of 0.01 microliter. Another problem arises from the fact that small-bore capillaries utilize relatively low flow rates of the order of 0.5 to 1.5 milliliters per minute, with the result that column efficiencies will decrease quite rapidly as the average linear velocity in the column departs from an optimum value (usually within the range from about 13 to 25 centimeters per second). Another problem arises because the volume of the inlet port for the sample must be quite small in relation to the volume of carrier gas flow through the system since, otherwise, an effect known as "band broadening" is experienced with disastrous results as respects constituent resolution. While this band broadening effect is not a particular problem with packed or wide-bore capillary columns (since the high flow rates of carrier gas flush the inlet chamber clean in a very short time interval), the relatively low flow ragtes encountered in capillary columns produce such severe band broadening effects as to render conventional inlet ports entirely unsatisfactory.

In an effort to counter certain of the foregoing deficiencies, it has become common in the operation of small-bore capillary columns to employ an inlet splitter. In general, the inlet splitter functions to vaporize the small quantity of sample in a much greater volume of carrier gas and to pass the vapor-gas mixture over the capillary column inlet so that only a small aliquot is introduced onto the column whereas the major portion of the mixture is vented to the atmosphere. In general, to insure good resolution in the chromatograph, it is essential that the injected sample be vaporized instantly and completely to the carrier gas, that no residual sample remains in the inlet chamber, that the vaporized sample be completely introduced on the shortest possible segment of the column, and that the sample be followed by pure carrier gas rather than carrier gas containing exponentially diluted sample. It is also highly desirable that the split to the column be essentially linear, to insure that the concentration of each component split to the column is a function only of its concentration in the injected sample.

In practice, reliable and accurate isolation of the split sample is not always effectively accomplished. Thus, it is a common experience of workers in this field that many compounds of interest in the original material are relatively labile with the result that rearrangement and degradation of the constituents within the chromatograph frequently result. It can also be demonstrated that the fractionation of the sample is not truly linear, and that the portion entering the capillary column is not identical in composition with the original bulk sample. Causes of these difficulties are many, including changes associated with rapid vaporization of the samples in the presence of hot metal surfaces, and the use of inexact splitting arrangements such as simple concentric tube splitters. As a consequence, despite the common use of inlet splitters in conjunction with the capillary chromatographic columns, the development of a truly reliable linear inlet splitter, by which substantially pure aliquot samples can be introduced to the capillary tube, is highly to be desired.

SUMMARY OF THE INVENTION AND OBJECTS

The present invention provides what now seems a simple solution to the problem of accurately and reliably introducing very small analysis samples to a capillary chromatographic column, through provision of an inlet splitter apparatus and method which avoids degradation or rearrangement of the sample and non-linearity of the split.

In general, the inlet splitter apparatus and method of the present invention provide substantially pure, linear sample aliquots for capillary gas chromatography. The splitter apparatus generally comprises a simple elongate body provided with two substantially cylindrical interior chambers or passages, each having inlet and outlet ends. A sample port and means to introduce a sample therethrough is provided at the inlet of one of the chambers (injection chamber) whereas the outlet of the other of the chambers (mixing chamber) receives the inlet end of the capillary chromatographic tube. In general, the outlet of the injector chamber coincides with the inlet of the mixing chamber. The body is further provided with means for sealingly supporting an elongate inert (glass) tubular liner for receiving the sample and transmitting it to the capillary chromatographic tube. Optionally, the inlet or injector chamber can be lined with an inert (glass) injector cap which has a relatively small instrument opening in an end wall, in axial alignment with the sample port. Heating means maintain a desired temperature of the body and with the separate chambers. The sample is introduced with a microliter syringe through the sample port and through a self-sealing septum so that it passes through the injector cap opening for deposit within the central core of the elongate tubular liner, within the heated inlet or injector chamber.

Carrier gas, introduced to the first or inlet chamber of the body, makes its way through the device by penetrating the annular space between the body and liner tube. When the injector chamber is optionally lined with a glass injector cap, this annular space is between the cap and liner tube. At the point of sample injection, the carrier gas picks up and vaporizes the sample and advances along the central bore of the elongate tubular liner to the second or mixing chamber. There, the intermixed carrier gas and vaporized sample are subjected to a rapid inversion or reversal of flow by means of inert (glass) baffles associated with the tubular liner so that thorough intermixing of the carrier gas and sample rapidly occurs. The mixed, blended sample emerges from the baffle means to an expansion zone within the second or mixing chamber, where a small portion is split to the capillary column. The remaining (major) portion of the gaseous mixture exits by way of an outlet port leading from the mixing chamber to the outside of the body.

In a preferred but optical embodiment of the invention, additional vaporization surface for the injected sample is provided in the form of a glass bead packing which partially fills the bore of the elongate tubular liner. The packing is generally in the form of very fine glass beads (Corning - 100 - 120 mesh) which are held in place by means of glass (or quartz) wool plugs inserted within the bore of the tubular liner. The glass wool plugs function to hold the glass beads in place and to assist the glass beads in providing an increased intermixing of the carrier gas and sample as they progress through the narrow passageways between the beads and the material of the plugs.

A particular feature of the present invention resides in the fact that the introduced sample contacts only inert surfaces within the elongate liner tube and baffles (including, when used, the glass bead packing), throughout the operations wherein it is instantly vaporized within the carrier gas, thoroughly intermixed with the carrier gas by reversal or inversion of flow, and directly introduced as a linear aliquot to the inlet end of the capillary chromatographic column. Degradation of the sample and nonlinearity of the split, the two most serious problems arising with splitting injectors, are therefore avoided. The inlet splitter of the present invention particularly insures that the hot carrier gas is intermixed with the introduced sample only within the inert core passage of the elongate tubular liner, to thereby insure against degradation of the injected sample. The inlet splitter of the present invention is also constructed to be demountable, particularly to permit periodic removal and cleaning of critical surfaces, e.g., the inert elongate liner tube and baffle. Such demountability is advantageous because it permits residual, non-volatile materials to be periodically removed from such surfaces so as to avoid degradation or catalysis to produce undesirable changes in subsequent sample injections, based on accumulated residues from previous injections. Cleaning is easily accomplished by use of solvents (e.g., concentrated nitric acid). It is also possible to render the inert glass parts even more inert by periodic treatment with silylanizing reagents such as hexamethyldisilylane, or one of the other silylanizing reagents.

It is accordingly an object of the present invention to provide an inlet splitter and fractionation method by which substantially pure sample aliquots of a high degree of linearity as respects the original sample, can be supplied in desired quantity to capillary chromatography columns in a rapid, controlled, reproducible fashion.

Another object of the invention is to provide an inlet splitter and method of the above character wherein any build-up of sample residues from previous sample injections is continuously diminished or eliminated so as to avoid sample degradations and rearrangements.

A particular object of the invention is to provide an inlet splitter apparatus and method of such character wherein all vaporization, mixing and splitting operations with respect to an introduced sample are carried out entirely within a nonreactive environment composed of an inert substance such as glass.

A further object of the invention is to provide an inlet splitter apparatus of such character which is easily and inexpensively fabricated and which is constructed in an economical manner for easy assembly and demountability of parts and fillers, thus facilitating periodic cleaning and/or treatments to enhance the inertness of the system.

Additional objects and advantages of the invention will appear from the following description in which illustrative embodiments have been set forth in detail in conjunction with the accompanying drawing.

BRIEF DESCRIPTION OF THE DRAWINGS

FIG. 1 is a partly schematic representation of one embodiment of a capillary gas chromatograph system, illustrating in section an inlet splitter according to the present invention.

FIG. 2 is a view partly in end elevation and partly in section along the line 2—2 of FIG. 1.

FIG. 3 is an exploded view in section illustrating the manner of assembly of the demountable components of the inlet splitter of FIG. 1.

FIG. 4 is a view in section along the line 4—4 of FIG. 3.

FIG. 5 is a like view along the line 5—5 of FIG. 3.

FIG. 6 is a view in section, similar to FIG. 3, illustrating another embodiment of the invention.

FIG. 7 is an exploded view in side elevation of the embodiment of FIG. 6, with portions broken away for clarity, and illustrating a procedure for assembly of the embodiment of FIG. 6.

DESCRIPTION OF PREFERRED EMBODIMENT

Figure 8:
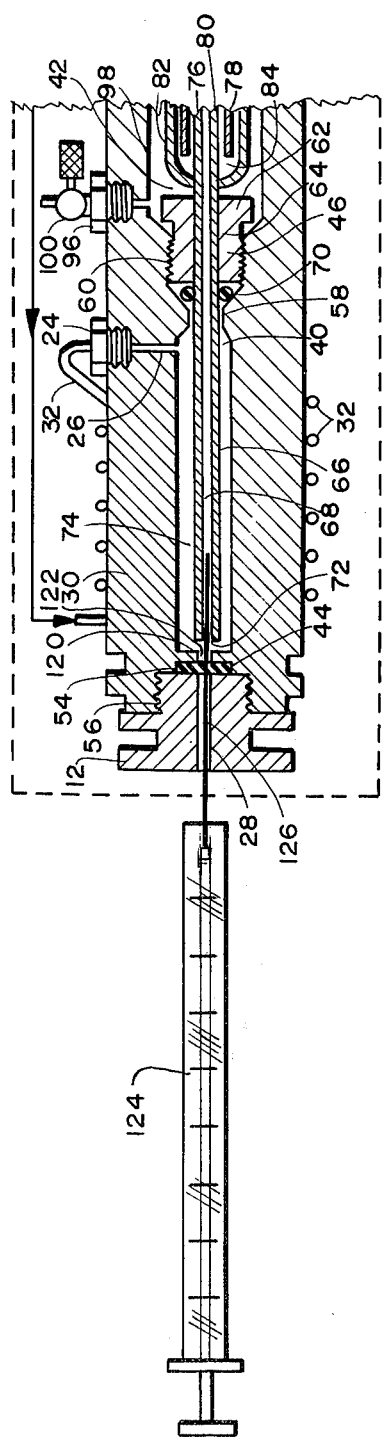
FIG. 8 is an enlarged fragmentary view, similar to FIG. 1, illustrating a further embodiment of the invention.

Referring to FIG. 1, the illustrated gas chromatography apparatus consists of four basic components: a carrier gas supply 4 including a flow control at 6 and 8, an inlet splitter 10 including a means 12 for introducing the sample, a chromatograph column 14 including a capillary tube 16, and a detector 18 including readout means 20, 22. As schematically represented in FIG. 1, the carrier gas is conveniently supplied from a compressed source through a pressure reducing valve means 6, 8 which control the input pressure on the apparatus and thus the flow rate and velocity of the carrier gas through the column. In some systems, the carrier gas enters the reference side of the detector 18, the output of which opposes that of the sensing side. This is common practice for differential type detectors, particularly thermal conductivity detectors, and serves to compensate for gradual changes in composition and temperature of the gas. From the reference, the carrier gas enters the inlet splitter through the port 24 and conduit 26. In other systems, not operated in the dual detector mode, the carrier gas might pass directly from the pressure reducing valve 6, 8 to the inlet splitter entrance port 24.

As hereinafter described in detail, a small liquid sample can be injected through the sample port or aperture 28 from which point it is swept into the capillary column 16 as an intermixed vapor (containing sample) wherein the non-volatile liquid sorbent coated on the inner surface of the capillary column effects retardation of the various components of the sample according to their vapor pressure and interaction with the sorbent. The separated components in the carrier gas then enter the detector 18 which may be of any suitable type, for example, a dual detector (as illustrated) or a more sophisticated ionization detector. Thereafter, as may be desired, the separated components can pass to a second detector in series, a mass spectometer, a fast-scan infrared spectrophotometer, to the atmosphere, or to collection apparatus for isolation. In the illustrated apparatus, reference and sensing elements for the detector 18 are opposed in conventional fashion in a suitable electrical bridge 20 so that with only carrier gas flowing through both sides of the detector, a straight base line results. When solute components enter the detector, a change in signal produces a differential output from the bridge proportional to the concentration or rate at which the solute component enters the detector. As is well known, the recorded output of the differential bridge produces a series of peaks reflecting the distribution or retardation process to which the solute components were subjected in their passage to the column, thus providing a chromatographic gas analysis.

Temperature control of the inlet splitter apparatus is obtained by use of cartridge heater elements 29. Thus, as particularly shown in FIG. 2, the inlet splitter apparatus may be fabricated as a dual splitter construction having identical inlet sections. In such construction, dual heating elements 28 are utilized to heat the elongate body 30, within which the inlet splitter components are assembled. In the illustrated apparatus, the carrier gas is conveniently preheated by wrapping the entire body assembly with an inlet conduit 32 through which the carrier gas is passed before it enters the carrier gas inlet port and conduit 24, 26. Preferably the inlet splitter assembly is provided with means to provide exterior heat to the entire unit, for example, a wrapping composed of glass insulating tape, an electrical heater, and finally glass wool insulation (not shown). Thus, as is well known, temperature control of the apparatus components enclosed by the dash line 39 of FIG. 1 is an important consideration in any gas chromatograph apparatus. Specifically, the minimum detector temperature for temperature control should be that of the column to prevent inadvertent condensation of solid components and resulting changes in concentration. In like fashion, the sample port temperature should be such as to permit rapid vaporization of sample solutes whose volatility is within the range of the chromatograph.

Referring now in detail to a single stage of the inlet splitter 10 shown in section in FIG. 1, the elongate body 30 is provided with two axially aligned, substantially cylindrical interior passages or chambers 40 and 42. The chamber 40 which may be termed the inlet or injector chamber, is of appreciably less diameter than the chamber 42 and has an open inlet end 44 and an enlarged outlet end 46. As illustrated in FIG. 1, the interior length of the inlet chamber is optionally provided with a lining in the form of a cylindrical injector cap 48 which has an end wall 50 provided with a relatively small instrument oening 52. The injector cap 48 is suitably constructed of an inert material such as glass or like material. The inlet end 44 of the injector chamber 40 is closed by means of a self-sealing cap or rubber septum 54, which is retained and held in place by means of the sample port or closure member 12. The latter is threaded in place within an enlarged bore 56 of the body, and serves to hold the septum 54 in place between the closure 12 and the end wall of the blass injector cap. As shown in FIG. 1, a sample port 12 is provided with a needle aperture 28 which is in alignment with the small instrument opening 52 of the injector cap, to permit insertion of a syringe needle for injection of a fluid sample through the septum 54. In this regard, the septum 54 is constructed of a material of the type commonly employed for sealing an opening to be punctured by a syringe needle, such as rubber, neoprene or silicone. Such components are commonly fabricated to be self-sealing, and to provide a satisfactory service life at operating temperatures (.e.g., 250° C for silicone, and 100° C or below for rubber or neoprene).

Referring again to FIG. 1, the outlet end of the chamber 40 is provided with a constriction at 58 which opens to an enlarged threaded bore 60 in which is received a threaded sealing and support element 62. As shown in the drawing, the member 62 has a central bore 64 which serves to support in axial fashion an elongate tubular liner 66, likewise constructed of an inert material such as glass. The liner 66 has an elongate central bore 68 which extends from the inlet end 44 of the injector chamber through the outlet 46 into the chamber 42. In this regard, as the outlet end of the inlet chamber 40 coincides with the inlet end of the chamber 42, both are designated by the same reference numeral 46. To insure a gastight seal as respects the elongate pathway or core 68 of the liner 66, an O-ring or like sealing member is positioned between the constriction 58 and threaded support member 62 so as to be compressed against the outer surface of the tubular liner 66. The sealing member 70 can be constructed of any suitable material such as rubber, neoprene or silicone or, for certain applications, a graphite O-ring or an asbestos string packing.

The elongate tubular liner 66 extends concentrically within the inert injector cap 48 so that its inlet opening 72 is adjacent but spaced from the small opening 52 in the end wall of the cap. The described arrangement provides an inert annular pathway 74 between the concentrically aligned inner surface of the injector cap 48 and the outer surface of the tube 66, which pathway is in direct communication with the inlet port 24 for the carrier gas. Thus, carrier gas at desired operating temperature and pressure sweeps into the inlet chamber 40 through the radially extending conduit 26, and passes through the annular pathway 74 to a point of flow reversal at the inlet end 72 of the elongate glass liner. In practice, this permits a sample to be introduced by means of a sample syringe directly through the needle aperture 28, septum 54, and injector cap opening 52 into the interior bore 68 of the elongate glass liner. In the heated environment of the inlet chamber 40, the sample is immediately vaporized within the carrier gas while entirely surrounding by the inert glass surface of the elongate tube 66, that is, within the core passage 68, thereby avoiding any possibility for degradation or rearrangement of the sample through contact with hot metal surfaces, as in prior inlet splitter designs. This is a feature of particular importance in insuring that the resulting chromatographic analysis of the injected sample is of high resolution and desired reproducible accuracy.

Following the initial mixing within the tubular liner 66, the vaporized sample is swept by the carrier gas to the outlet end 76 of the core passage 68, where it is directed against the surface of a rearwardly facing inert glass cup or baffle member 78. The function of the cup 78 is to cause a rapid inversion or reversal of the direction of flow within a zone of consequent turbulent intermixing of the vaporized sample and carrier gas, represented at 80. Thereafter, through impingement on the inner surfaces of a forwardly directed inert glass cup or baffle 82, the intermixed vapor and carrier gas undergo a further inversion or reversal of direction in the zone 84, causing a further thorough mixing of the vaporized sample and carrier gas. As the intermixed gases pass forward through the baffle 82, further turbulent intermixing is caused by the constriction 86 in the wall of the baffle, as the gases pass forwardly into an expansion zone 88 within a terminal portion 90 of the baffle.

In general, the described baffle means 78, 82 and 90 provide a plurality of mixing and expansion chambers within the outlet chamber 42. The overall function of the baffle means is to insure that a uniformly blended mixture of carrier gas and sample is discharged to the expansion zone 88, for subsequent splitting to the inlet end 92 of the small-bore capillary chromatograph column 16. It will be appreciated that only a very small portion of the blended gaseous mixture passes to the interior of the capillary column, the excess being vented through a surrounding buffer zone 94 by means of a discharge port 96. In the illustrated apparatus, the excess gas passes through the radial extending pathway to a discharge control means 100, such as a needle valve, which can be conveniently adjusted to control the proportion of gas discharged from the outlet chamber. Alternatively, the discharge control means 100 might take the form of a fixed orifice provided with a restrictor of desired size. Thus, by appropriate adjustment of the needle valve (or in the case of a fixed orifice outlet, by selection of a given restrictor), the ratio of excess gas to the sample split to the capillary column (i.e., "the split ratio") can be easily and effectively controlled.

As will be understood by one in this art, the ratio of the diameter of the chamber 42 to that of the capillary bore 16 can also provide a means for controlling the split ratio. In general, it is desirable that the discharge control 100 be kept within the heated zone as represented within the dash line 39 to avoid condensation and a change in the desired split ratio.

In accordance with the invention, it is essential that the elongate liner and its associated baffle means, as generally represented at 66, be constructed of an inert material such as glass, or like material. Specifically, such construction insures that the injected sample will contact only glass or a like inert surface until such time as the small intermixed sample portion has been split to the inlet end of the capillary column 16. The injected sample is thus protected against degradation or rearrangement from the instant of injection through the sample port 12, during the intermixing within the core passage 68 and sweeping with the carrier gas through the elongate tubular unit 66, until such time as the sample aliquot to be analyzed actually passes into the capillary column 16 of the chromatograph. The described degree of protection for the injected sample is particularly important with a labile analysis mixture which is known to undergo degradation or rearrangement as a result of vaporization on hot metallic surfaces, such as the stainless steel or copper components normally employed.

As respects construction and assembly, it will be understood that the inert gas components 48 and 66 are easily fabricated on conventional equipment for such purpose such as a glass lathe. For example, in the fabrication of the baffle means 78 and 82, the outer cup baffle 82 may be fabricated as an integral cylindrical component on the end of the elongate tube 66. Thereafter, the small inner cup baffle 78 may be deposited within the baffle 82 so as to surround the outlet 76 of the tube. Thereafter, the construction 86 can be formed within the wall of the baffle 82 to hold the small cup baffle in place. Following assembly into the inlet splitter 10, the cup baffle 78 has a certain freedom of axial movement within the confines of the cup baffle 82 and the constriction 86. Thus, upon operation of the system, the rapid flow of the intermixed carrier gas and sample pushes the cup baffle 78 away from the outlet 76 of the tube against the baffle constriction 86. Moreover, in an arrangement of the inlet splitter wherein the unit 10 is positioned vertically on top of the capillary column, the cup baffle will assume a normal gravity position in contact with the constriction 86. It will be understood, however, that these are practical considerations and that the principal function of the baffle means is to effect a rapid inversion and consequent turbulent intermixing of the vaporized sample and carrier gas, so that a uniformly blended gaseous mixture can be linearly split to the inlet end of the capillary column 16.

As will be apparent from FIG. 1, the inlet splitter 10 is constructed to be demountable so that the parts may be periodically disassembled for cleaning or replacement. Demountability is particularly advantageous as respects the inert components forming the nonreactive pathways for the injected sample, since it permits residual nonvolatile materials to be periodically removed by cleaning in solvents, and also enables such surfaces to be rendered even more inert by silylanizing. Thus, upon removal of the sample port 12 and septum 54, the glass injector cap 48 is easily removed for cleaning or replacement. In like fashion, the capillary column 16 is demountably assembled within the end closure 102, which is easily removed from within the threaded outlet 104 of the mixing chamber 42. Demountability of the capillary column may also be achieved by any suitable means, such as the apertured nut 106 and sealing means 108.

Following removal of the capillary column and support 102 from the outlet end 104 of the inlet splitter, the tubular liner 66 can be disassembled by removing the threaded sealing and support element 62 from the threaded bore 60. The tubular liner may then be separated from the support element 62 for cleaning, or replacement, in the same manner as the glass cap 48. When the cap and liner components 48 and 66 are constructed of glass, cleaning is easily accomplished by immersion in suitable solvents such as nitric acid or any other appropriate solvent. If desired, the glass surfaces of the cap and liner components can thereafter be silylanized, prior to reassembly. It is recognized that residues from previous injections can accumulate in the injection chamber, where they degrade and frequently catalyze a variety of undesirable changes in subsequent injections. The benefits of use of inert materials such as glass are thus enhanced, if the inert surfaces are periodically treated with a silylanizing reagent such as hexamethyldisilylane (HMDS) or one of the other silylanizing reagents.

The overall operation of the inlet splitter shown in FIG. 1, in supplying a linear aliquot of sample and carrier gas to a small-bore chromatograph, can now be described as follows:

Assuming the use of dual injector design for a commercial chromatograph (viz., Model 5700 chromatograph as manufactured and sold by the Hewlett-Packard Corporation, Palo Alto, Calif., the sample (0.1 to 10.0 microliters) is introduced with a microliter syringe through the needle aperture 28, and through the rubber septum 54 and the opening 52 in the inert injector cap 48. Upon injection of the sample, the sample material is deposited within the central bore 68 of the elongate glass liner 66. Preheated carrier gas introduced at the inlet port 24, finds its way through the annular space 74 between the inert injector cap 48 and the tubular liner 66. From this annular pathway, the carrier gas proceeds to the inlet opening 72 of the tubular liner where it picks up and assists in vaporization of the injected sample within the heated interior surfaces of the core passage 68. Thereafter, the intermixed sample and carrier gas exit through the outlet end 76 of the tubular liner where they are subjected to repeated, turbulent reversals of gas flow through contact, first, with the inner cup baffle 78 and then, with the outer cup baffle 82. The rapid flow rate of the carrier gas and sample coupled with the inversion of flow, causes a thorough intermixing and blending of the gases prior to their discharge into the expansion zone 88. Within the expansion zone, a small aliquot of the mixed, blended sample is split to the inlet end 92 of the chromatograph column 16, while the remaining major portion of the blended carrier and sample gases exit by way of the outlet port 96 and needle valve 100. By controlling the proportion of gas discharged through the needle valve 100, the split ratio is easily adjustable over a wide range (e.g., 5:1 to 1000:1). For example, with a 1.0 microliter injection sample and a split ratio of 100:1, an analysis sample of 0.01 microliters is introduced to the column 16.

In the described installation, the dimensions of the needle aperture may be 1.0 mm, permitting syringe injection of a very small sample of the order of 0.01 microliter. Within the inlet splitter 10, the glass injector cap may provide an interior diameter of 5.9, which in conjunction with an outer diameter of the elongate tubular liner 66 of 5.5 mm provides an annular cross section of the flow path approximating 3.94 mm². Flow rates of carrier gas within the flow path 74 and through the interior bore 68 of the tubular liner (interior diameter, 1 to 2 mm), may approximate 30 to 200 ml/min. As respects the outlet chamber 42, the inside diameter may approximate 20 mm, whereas the inside diameter of the expansion zone 88 may approximate 7 to 10 mm. Flow rates within the expansion chamber will thus approximate 30 to 200 ml/min. The internal capillary diameter of the chromatograph column 16 may approximate 0.25 to 0.75 mm. Flow rates within the capillary column are therefore of the order of 0.5 to 5.0 ml/min. However, as previously noted, flow rates that cause the average linear velocity of the column to depart from an optimum value (i.e., as previously noted, within the range from about 13 to 25 cm/sec.) are not as efficient for accurate chromatographic analysis as are flow rates close to the optimum value. Thus, by way of specific example, the flow rate in a capillary column of 0.25 mm inside diameter should approximate 0.8 ml/min., or 15 to 20/cm/sec.

Referring now to FIG. 6, a modified embodiment of the inlet splitter is shown wherein means are provided within the inlet passages to increase the vaporization surface and mixing potential of the system. Thus, as particularly shown in FIG. 6, the bore 68 of the tubular liner 66 is substantially filled with an inert subdivided packing 110, which preferably is in the form of very fine beads constructed of glass or like inert material. In the illustrated embodiment, the glass beads 110 occupy the internal space within the bore 68 of the liner 66 from a point approximately midway along its length to a point adjacent the outlet end 76 of the tubular liner. The glass beads are held within this space by means of two inert porous plugs, including a first plug 112 which substantially fills the inlet end of the bore 68 and a second plug 114 which substantially fills the zone 80 within the rearwardly facing cup member 78. The inert plugs 112, 114 can be constructed of any available inert filament material such as glass wool or quartz wool, the essential requirement being that the plugs hold the glass beads 110 in place while providing inert passageways for movement of the carrier and sample gases. While use of glass wool plugs is satisfactory for most applications, quartz wool provides the advantage of being somewhat less adsorptive.

FIG. 7 illustrates one procedure for construction or assembly of the modified embodiment of FIG. 6. Thus, as illustrated, the tubular liner is constructed from two separate components 66a and 66b. Using conventional glass blowing techniques, the short section 66b is sealed internally to the end portion 116 of the cup 82 and an aperture is blown through the portion 116 so as to be in alignment with the bore of the section. The elongate portion 66a of the tubular liner is then ring-sealed to the cup 82 so that the bore 68a is in axial alignment with the bore 68b of the inner tube 66b. The inert plug 114 is now placed within the cup member 78 and the unit comprising the cup and porous plug is inserted within the open end of the cup 82 until the plug 114 is slightly compressed about the outlet end 76 of the interior tube 66b. Inward projections or dimples 118 are now pushed into the wall of the outer cup 82 to retain the inserted cup 78 within the mixing zone 84, and to define the expansion zone 88. The inert subdivided packing material, viz., tiny glass beads, is now poured into the open end of the tubular liner 66 until the bore of the inner segment 66b is entirely filled with beads, and the bore of the outer segment 66a is filled to approximately ⅓ to ½ its length. The second inert plug 112 is now pushed down the open end of the tubular liner segment 66a to hold the glass beads 110 in place. Thereafter the liner components, containing the glass beads, are inserted within the elongate body 30 in the manner previously described.

Variations are possible in the form and size of the inert subdivided packing material 110. Specific materials include finely subdivided bead packings of glass or quartz and, for certain applications, coarse silica sands. A particularly satisfactory form of packing is comprised of very fine glass beads, for example, as manufactured by Corning Glass under the designation 100–120 mesh. By "100–120 mesh" is meant particle size as determined by screening (U.S. Standard Sieve Series) whereby 100% of the beads pass through a 100-mesh sieve whereas 100% of the glass beads are retained on a 120-mesh sieve. While this particular bead size is not deemed to be critical to the success of the packing, it has been determined that larger bead sizes will decrease the efficiency of the packing as respects the mixing of the gases and providing vaporization surfaces for the sample gas. In like fashion, smaller bead sizes tend to undesirably increase the pressure drop across the system.

It will be appreciated that the described embodiment of the tubular liner, containing the inert beak packing or filler 110, is capable of being periodically removed from the body 30 for cleaning in nitric acid or other appropriate solvent, in the manner previously described. The filler liner can also be silylanized, prior to assembly, to prevent the accumulation of undesired residues on the bead packing 110 or within the inert porous plugs 112 or 114.

In general, the packing or filler 110 functions to provide additional inert vaporization surfaces for the injected sample, within the inlet portions of the inlet splitter. For example, a multiplicity of very fine glass beads 110 within the tube 66 serves to enlarge the inert surface area within the heated environment of the bore 68 thereby increasing the efficiency of vaporization of the sample and carrier gases. The multitude of inert filaments within the plugs 112 and 114 likewise serve to increase the vaporization surface for the intermixed gases. The tortuous pathways through the inert wool plugs and bead packing 110 additionally provide an increased mixing potential, to insure a thorough intermixing of the carrier gas and the sample vapors. The inert filler or packing thus functions to increase both the vaporization and mixing potential of the inlet splitter, in accordance with the present invention.

In the embodiments of FIGS. 1 and 6, the hot carrier gas is introduced to the system through an inert annular passageway formed between the glass injector cap 48 and the glass tubular liner 66. While introducing the carrier gas through an inert annular pathway in this manner additionally protects against degradation of the injected sample, this precaution is not essential to the practice of the invention. As a practical matter, it is only necessary that the sample be introduced sufficiently far into the interior of the inert core passages 68 of the tubular liner, that possibility of contact of the sample gas with the hot metal of the body is avoided. This feature of the invention is illustrated with reference to FIG. 8.

Referring to FIG. 8, the construction and arrangement of the parts is identical to that shown in FIG. 1 except that the cylindrical glass injector cap has been omitted. In its place, at the inlet end of the chamber 40, the body is provided with an inwardly directed radial flange 120 which is centrally provided with a relatively small instrument opening 122. The radial flange 120 functions as a retaining means for the self-sealing rubber septum 54, which is held in place between the flange and the sample port or closure 12. The sample is introduced, as before, by means of a microliter syringe 124 having a long hollow injection needle 126. The needle 126 penetrates the rubber septum 54 and passes through the opening 122 to the interior core passage 68 of the elongate tubular liner 66. It will be understood that the preheated carrier gas sweeps through the annular space 74 between the walls of the inlet chamber 40 and the tubular liner 66 and into the core passage 68. This movement of the carrier gas prevents any possibility of the sample from coming into contact with the hot metal walls of the body and functions to immediately pick up the injected sample and to carry the same through the flow reversing baffle means within the mixing chamber 42, where a small aliquot of the intermixed sample and carrier gases is split to the inlet end of the chromatograph column in the manner previously described. In general operation, therefore, the embodiment of FIG. 8 does not differ from the operation of the embodiment of FIG. 1 since, in both instances, the sample material is deposited well within the inert environment of the central bore 68 of the elongate glass liner 66, thus avoiding any possibility for reactions within the splitter which might degrade or rearrange the constituents of the introduced sample.

Figure 9:
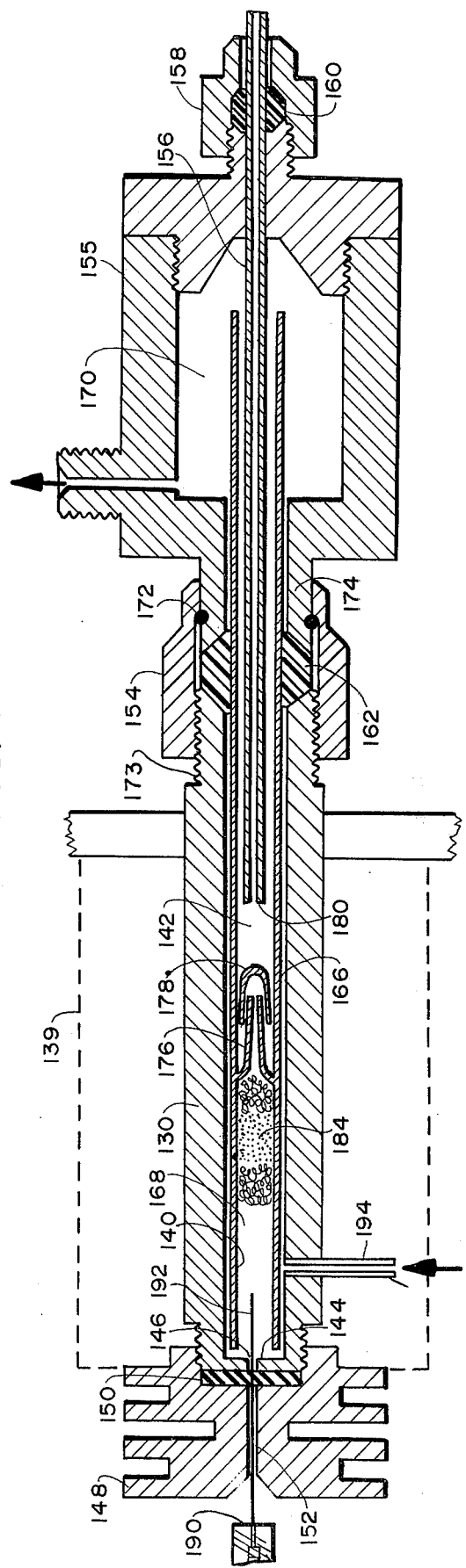
FIG. 9 is a partly schematic representation, similar to FIG. 1, illustrating in section a still further embodiment of the invention.

Referring to FIG. 9, a further modified embodiment of the inlet splitter is shown wherein means are provided to adapt the concepts of the present invention for use with commercial ¼inch (6.35 mm.) heated inlets as normally designed for ¼ inch packed columns. Thus, 130 represents an elongate inlet attachment or body for a commercial unit of this type. Again, conventional means can be provided for temperature control of the apparatus, as represented by the dotted line enclosure 139. The body 130 is provided with a substantially cylindrical interial passage or chamber which includes both an inlet or injector chamber 140 and a mixing chamber 142. At the inlet end, the body is provided with an end wall or closure 144 which is provided with a small instrument opening 146. As illustrated, the inlet end of the body 130 can be suitably threaded to receive a sample port or end closure member 148 which serves both to hold the self-sealing rubber septum 150 in place and to provide a needle aperture 152 for insertion of a microliter syringe.

At its opposite or outlet end, the body 130 can be threaded to receive connecting means 154 for holding the splitter body on the inlet end of a chromatograph column 155, in concentric relation to a capillary tube 156 associated with the chromatograph. The latter is held in place by suitable means such as a collar 158 and graphite ferrule 160, and can extend a substantial distance into the outlet chamber of the splitter body 130.

As illustrated in FIG. 9, the connection between the splitter body 130 and chromatograph column 155 includes a large diameter graphite ferrule 162 which serves to axially support an elongate tubular liner 166, which may be constructed (as before) of an inert material such as glass. The liner 66 generally includes an elongate central bore 168 which extends from the inlet end of the body chamber 140 through the supporting ferrule 162 and into an outlet chamber 170 associated with the inlet end of the chromatograph. As shown, a retaining nut 154 cooperates with the graphite ferrule 152 to insure a gastight seal as respects the interior chambers of the splitter body 130 and the chamber 170 in the chromatograph. Upon tightening the nut 154 on a threaded extension 173 on the body, a retaining ring or keeper 172 is engaged, drawing the tubular extension 174 toward the body extension 173 to compress the graphite ferrule 162 therebetween. Such connection provides an effective seal between the glass liner 166 and the body extension 173 and also between the liner 166 and the chromatograph tubular extension 174.

Internally, the elongate tubular liner 166 is provided with flow directing baffle means in the form of an integral flow restricting glass member 176 which is coupled with a rearwardly facing inert glass cup or baffle member 178. The latter functions to create a rapid inversion or reversal of the direction of flow and a consequent turbulent intermixing of the vaporized sample and carrier gas entering the mixing chamber 142. Thereafter, the blended mixture of carrier gas and sample is split to the inlet end 180 of the small-bore capillary chromatograph column 16. As previously described, only a very small portion of the blended gaseous mixture actually passes to the interior of the capillary column, the excess being vented through the outlet end of the tubular liner 160 to the chamber 170. The excess gas is then discharged through the splitter outlet port 180, which may include a discharge control means (not shown) similar to the discharge control 100 previously described. The purpose of the discharge control is to provide means for adjusting the proportion of gas discharged from the outlet chamber and thereby to establish the desired split ratio.

As further illustrated in FIG. 9, the interior of the elongate tubular liner 166 may be provided with additional means to increase the vaporization surface and mixing potential of the system. Thus, the inlet end of the bore 168 can be substantially filled with an inert subdivided packing 184, for example, very fine beads of glass or like inert material. For such purpose, inert porous plugs 186, 188 can be provided on either side of the glass beads to hold the same in place. As noted previously, such plugs can be fabricated of glass or quartz wool or other suitable inert filament material.

In the operation of the modified inlet splitter shown in FIG. 9, the sample can be introduced by means of a conventional microliter syringe 190. Specifically, the needle 192 of such device is inserted through the needle aperture 152, rubber septum 150, instrument opening 146, and into the central bore 68 of the elongate glass liner 166 within the splitter body. In general, the needle 192 should be thrust well into the interior of the glass liner to insure that the sample material is deposited at a point sufficiently within the protective inert environment of the tubular liner to avoid any possibility for the sample coming into contact with the hot metal surfaces of the splitter body 130. To assist in this function, the preheated carrier gas passes into the splitter body through the inlet port 194, and through the annular space 148 between the walls of the inlet chamber 140 and the elongate tubular liner 166 to the inlet end of the elongate liner 166. There the carrier gas reverses direction and sweeps through the core passage 168 of the tubular liner 166 to pick up and assist in the vaporization of the injected sample within the core passage 168. Upon coming into contact with the multiplicity of very fine glass beads 184, the injected sample is further vaporized and intermixed with the carrier gas. The multitude of inert filaments within the plugs 186 and 188 likewise serve to increase the vaporization surface for the intermixed gases, and the thorough intermixing of the injected sample and carrier gas. Upon coming into contact with the restricting baffle 176, the rate of gas flow is increased somewhat for impingement and reversal of flow within the cup baffle 178, following which the thoroughly mixed carrier gas and sample passes into the expansion zone 142 for splitting on the end 180 of the capillary tube 156.

When the optional glass injector cap is omitted, as in FIG. 9, the elongate tubular liner 166 can be somewhat larger (e.g. 6 mm o.d. glass tubing through its entire length); also, the size of cup baffle 178 can be increased (e.g., 4 mm o.d. and 2.5 mm i.d.).

In general, the inlet splitter of FIG. 9 functions to deliver substantially pure aliquots possessing a high degree of linearity as respects the original sample, to the inlet end of the capillary chromatographic column, for splitting in a rapid, controlled reproducible fashion. As in the previous embodiments, the device of FIG. 9 functions to achieve vaporization, mixing and splitting of an introduced sample entirely within a nonreactive environment, comprising the inert glass liner 166 and associated inert baffles 176, 178 and retained packing 184, 186, 188.

It will be understood that the above description is intended to be merely illustrative of representative systems of apparatus and their operation, and that many variations are possible within the scope of the present invention. For example, while glass constructions of the tubular liners 66 and 166 have been described (also for the injector cap 48 and baffles 78, 86, 176, 178), other inert materials may likewise be satisfactorily employed, for example, various high temperature plastics of inert composition as respects the sample undergoing analysis. Variations in the particular arrangement of the inert baffle means 78, 82, 90 or 176, 178, in the form, particle size and arrangement of the packing 110, 184 and plugs 112, 114 or 186, 188, to achieve the desired rapid inversion and intermixing of the carrier gas and vaporized sample, are also contemplated. These and other variations in the construction and in the method of use of the described inlet splitter apparatus and method, are clearly within the skill of one in this art and within the intended scope of the invention.

I claim:

1. In an inlet splitter for a gas chromatograph, a body having aligned injector and mixing chambers, means to heat said body and said chambers, elongate means forming an inert pathway between said injector and mixing chambers, said elongate means having an inlet in said injector chamber, and a baffled outlet opening to an expansion zone in said mixing chamber, means injecting an analysis sample into the inert pathway of said elongate means, means introducing a continuous flow of carrier gas to said inert pathway of said elongate means, said carrier gas serving to pick up, vaporize and convey injected sample through said electronic means and baffled outlet to said expansion zone, means forming a part of a gas chromatograph to withdraw a linear aliquot of intermixed sample and carrier gas from said expansion zone, and discharge means to effect removal of excess quantities of intermixed sample and carrier gas from said expansion zone and mixing chamber.

2. An inlet splitter as in claim 1 wherein at least a portion of said inert pathway within said elongate means is substantially filled with an inert subdivided packing.

3. An inlet splitter as in claim 2 wherein said inert subdivided packing is in the form of a very fine inert glass beads.

4. An inlet splitter as in claim 3 wherein said glass beads are of a particle size whereby 100% pass through a 100-mesh screen and 100% are retained on a 120-mesh screen, U.S. Standard Series.

5. An inlet splitter as in claim 2 including plug means formed of inert filaments to hold said inert packing in place within the inert pathway of said elongate means.

6. An inlet splitter as in claim 5 wherein said inert plugs are formed of glass wool.

7. An inlet splitter as in claim 1 wherein said elongate means and the injector and mixing chambers of the body are in substantially axial alignment with one another.

8. An inlet splitter as in claim 7 wherein said elongate means comprises an elongate glass tube with flow baffles at the end thereof.

9. An inlet splitter as in claim 8 including means to sealingly support said elongate glass tube in axial alignment within said injector and mixing chamber.

10. An inlet splitter as in claim 1 wherein the baffled outlet end of said elongate means includes an inner flow reversing cup means and an outer flow reversing cup means which cooperate to effect intermixing of the carrier and sample gases and discharge of the same into said expansion zone.

11. An inlet splitter as in claim 10 wherein all components of said elongate means are integrally constructed of glass.

12. An inlet splitter as in claim 1 wherein said means introducing a continuous flow of carrier gas includes flow control means regulating the pressure of the gas and conduit means extending through said body to said injector chamber.

13. An inlet splitter as in claim 1 wherein said means forming part of a gas chromatograph is the inlet end of a capillary chromatograph column extending into and positioned within said mixing chamber.

14. In an inlet splitter for a gas chromatograph, a body having aligned injector and mixing chambers, means to heat said body and said chambers, elongate means forming an inert pathway between said injector and mixing chambers, said elongate means having an inlet end in said injector chamber and a baffled outlet end forming an expansion zone in said mixing chamber, means lining said injector chamber and forming an inert annular pathway surrounding said elongate means, means injecting an analysis sample into one of said inert pathways of said injector chamber, means introducing a continuous flow of carrier gas to said pathways to flow through said inert annular pathway and into said inert elongate pathway, said carrier gas serving to pick up, vaporize and convey injected sample through said elongate means and baffled outlet to said expansion zone, means forming a part of a gas chromatograph to withdraw a linear aliquot of intermixed sample and carrier gas from said expansion zone, and discharge means to effect removal of excess quantities of intermixed sample and carrier gas from said expansion zone and mixing chamber.

15. An inlet splitter as in claim 14 wherein said means lining the injector chamber includes an end wall having a small instrument opening therein for injection of said analysis sample.

16. An inlet splitter as in claim 14 wherein all components of said lining means are constructed of glass.

17. A substantially nonreactive linear inlet splitter for a gas chromatograph, comprising an elongate body, said body being provided with first and second substantially cylindrical interior passages, each having inlet and outlet ends, the outlet end of said first interior passage coinciding with the inlet end of said second interior passage, said second interior passage being of sufficient diameter to axially receive the inlet end of a chromatograph column, said body having a relatively small instrument opening adjacent the inlet end of said first interior passage, a self-sealing septum adjacent said instrument opening, removable closure means for the end of said interior passage, said closure means having a needle aperture therein in alignment with the instrument opening in said body to thereby facilitate introduction of an analysis sample, substantially inert tubular liner means extending from a position closely adjacent said instrument opening to a position within said second interior passage means, said inert tubular lining means being removably supported in axially aligned relation within said first and second interior passages by demountable sealing means associated with said body, said tubular lining means providing a substantially inert pathway within said tubular liner means, means for introducing carrier gas to said inert pathway within said tubular liner so that the same passes through and along the length of said pathway within said tubular liner means, the portion of the tubular liner means within said second interior passage of the body being provided with baffle means to effect simultaneous reversal of direction and mixing of carrier and analysis sample gases passing therethrough, removable closure means for the outlet end of second interior passage of the body, said last named means including means to axially receive and support the inlet end of said chromatograph column so that the latter extends into the interior of said interior passage of the body, and means for controllably withdrawing excess amounts of intermixed carrier and analysis sample gases from said second interior passage of the body, whereby a sample introduced through said needle aperture is introduced within said inert pathway within said tubular liner where it is immediately picked up by carrier gas, intermixed with the same and introduced directly as a linear aliquot to the inlet end of said chromatograph column with contact being had only with the inert surfaces of said tubular liner.

18. An inlet splitter as in claim 17 wherein said elongate body is provided with heating means to establish a temperature within said first and second interior passages which is optimum for sample vaporization and mixing with said carrier gas.

19. An inlet splitter as in claim 17 wherein said demountable sealing means comprises a compressible sealing ring and a cooperating threaded member for supporting said inert tubular liner means.

20. An inlet splitter as in claim 17 wherein said means for introducing carrier gas includes a radially extending conduit in said body and means for preheating the carrier gas introduced to said conduit means.

21. An inlet splitter as in claim 18 wherein said means for preheating the carrier gas comprises tubular conduit means encircling said body so as to be heated by said heating means for the body.

22. An inlet splitter as in claim 17 wherein said chromatographic column has a diameter substantially less than the diameter of said second substantially cylindrical interior passage, the ratio of said diameters serving to control the aliquot portion of intermixed sample and carrier gas introduced to said chromatograph column.

23. An inlet splitter as in claim 17 wherein said means for controllably withdrawing intermixed carrier and sample gas comprises a radial discharge conduit leading from said second interior passage to the exterior of said elongate body, and means cooperating therewith for controlling the proportion of intermixed carrier gas and sample discharged through said radial discharge conduit.

24. A substantially nonreactive linear inlet splitter for a gas chromatograph, comprising an elongate body, said body being provided with first and second substantially cylindrical interior passage, each having inlet and outlet ends, the outlet end of said first interior passage coinciding with the inlet end of said second interior passage, said second interior passage being of sufficient diameter to axially receive the inlet end of a chromatograph column, a substantially inert injector cap lining said first interior passage, said injector cap having an end wall with a relatively small instrument opening adjacent the inlet end of said first interior passage, a self-sealing septum adjacent the end wall of said inert injector cap, removable closure means for the end of said interior passage, said closure means having a needle aperture therein in alignment with the instrument opening in said inert injector cap to thereby facilitate introduction of an analysis sample within said injector cap, substantially inert tubular liner means extending from a position closely adjacent said instrument opening within said injector cap to a position within said second interior passage means, said inert tubular lining means being removably supported in axially aligned relation within said first and second interior passages, said injector cap and tubular lining means cooperating within said first interior passage means to provide a substantially inert annular pathway surrounding said tubular lining means and communicating with a substantially inert pathway within said tubular liner means, means for introducing carrier gas to said annular pathway between the injector cap and tubular liner so that the same passes through the pathway within said tubular liner means, the portion of the tubular liner means within said second interior passage of the body being provided with baffle means to effect simultaneous reversal of direction and mixing of carrier and analysis sample gases passing therethrough, removable closure means for the outlet end of second interior passage of the body, said last named means including means to axially receive and support the inlet end of said chromatograph column so that the latter extends into the interior of said interior passage of the body, and means for controllably withdrawing excess amounts of intermixed carrier and analysis sample gases from said second interior passage of the body, whereby a sample introduced through said needle aperture is immediately picked up by carrier gas, intermixed with the same and introduced directly as a linear aliquot to the inlet end of said chromatograph column with contact being had only with the inert surfaces of said injector cap and tubular liner.

25. An inlet splitter as in claim 24 wherein said inert tubular liner means is provided with an outlet end positioned intermediate the ends of said second interior passage, first rearwardly extending inert cup means surrounding said outlet end, and second forwardly facing inert cup means surrounding said outlet end and said rearwardly facing cup means, said cup means providing mixing chambers for effecting reversal of direction and mixing of said carrier and sample gases passing through said inert tubular liner means.

26. An inlet splitter as in claim 25 wherein said second forwardly facing cup means has a forwardly extending cylindrical portion which forms an expansion and splitting chamber surrounding the inlet end of said chromatograph column.

27. An inlet splitter as in claim 24 wherein said injector cap and inert tubular liner means are fabricated of glass.

28. A glass inlet splitter for providing substantially linear sample fractionation for a capillary gas chromatograph, comprising an elongate body having at least two axially aligned substantially cylindrical interior passages, the first one of said interior passages having a sample receiving inlet end and a gas delivery outlet end, the second one of said interior passages having an inlet end coinciding with the outlet end of said first interior passage and an outlet end in substantially axial alignment with the inlet end of said capillary gas chromatograph, means for delivering an analysis sample to said first interior passage, said last named means including an apertured sample port and a self-sealing septum, means for introducing the carrier gas to said first interior passage including conduit means in said elongate body adjacent the outlet end of said first interior passage, means for mixing a sample with the carrier gas for delivery to said second interior passage, said mixing and delivery means including an elongate glass tube extending between said first and second interior passages and a glass injector cap lining the interior surfaces of said first interior passage, said injector cap having an end wall with a relatively small instrument opening in axial alignment with the aperture in said sample port, mounting and sealing means positioned in the coinciding outlet and inlet end of said first and second interior passages, said mounting and sealing means supporting said elongate glass tube in axial aligned relation within said first and second interior passages, mounting and sealing means closing the outlet end of said second interior passage, said last named means supporting said capillary chromatograph column so that the inlet end thereof is positioned within said second interior passage, glass baffle means supported within said second interior passage adjacent an outlet end of said elongate glass tube, said glass baffle means including an outer forwardly directed substantially cylindrical cup means and an inner rearwardly directed cup means, said rearwardly directed cup means surrounding an outlet end of said glass tube so as to effect mixing and reversal of direction of gases discharged by said elongate glass tube, said outer forwardly directed cup means surrounding said inner cup means so as to effect a mixing and reversal of gases discharged from said inner cup means, said outer cup means including a substantially cylindrical portion concentrically surrounding the inlet end of said capillary chromatograph column, and means for controllably withdrawing excess amounts of intermixed carrier gas and sample from said second interior passage, whereby sample introduced through said sample port is picked up by carrier gas adjacent the small instrument opening of said glass injector cap, intermixed with the same within said elongate glass baffle means and introduced directly as a linear aliquot to the inlet end of said capillary chromatograph with contact being had only with the inner surfaces of the injector cap, elongate tube and baffle means.

29. An inlet splitter as in claim 28 wherein said elongate glass tube and said glass baffle means are integrally constructed to insure an inert path of travel of said sample from said sample port to said capillary chromatograph column.

30. An inlet splitter as in claim 28 wherein said sample port and said respective sealing and mounting means are demountable to permit removal and cleaning of said glass injector cap, elongate glass tube and glass baffle means.

31. An inlet splitter as in claim 28 wherein said means for controllably withdrawing excess amounts of intermixed carrier gas and sample comprises a valved outlet port communicating through said elongate body with said second interior passage.

32. An inlet splitter as in claim 28 wherein said elongate glass tube is partially filled with an inert subdivided glass bead packing, said glass bead packing filling a zone within said elongate glass tube extending from a point within said first interior passage to a point within said second interior passage.

33. In a linear fractionation method for providing substantially pure sample aliquots for capillary gas chromatography, the steps of preheating a stream of carrier gas, introducing said stream of carrier gas to an inner inert core passage, heating said inner inert core passage to maintain a desired elevated temperature of said carrier gas, introducing an analysis sample to said stream of carrier gas within said inner inert core passage to flow with said stream of carrier gas through said core passage, said carrier gas serving to vaporize said sample and thereby form a mixed gaseous stream containing vaporized sample and carrier gas, introducing said mixed gaseous stream to an inert tortuous pathway wherein the direction of flow of said mixed gaseous stream is reversed in such fashion as to obtain a substantially complete turbulent mixing of said vaporized sample and carrier gases, and directing a predetermined volume of hot intermixed sample and carrier gases to the inlet of a capillary gas chromatograph to thereby cause separation of a desired aliquot of the same for capillary chromatographic analysis, the vaporization and intermixing of said sample and the separation of said desired aliquot of intermixed sample and carrier gases taking place wholly within the inert nonreactive environment of said inner inert core passages and said inert tortuous pathway.

34. A method as in claim 33 wherein enhanced vaporization and intermixing of said sample gas within said carrier gas is obtained in the presence of an inert finely divided inert filler within said inner inert core passage.

35. A method as in claim 33 wherein the rate of flow of intermixed sample and carrier gases passing into and through said capillary gas chromatograph is within the range from 0.5 to 10 milliliters per minute whereas the rate of flow of said stream of carrier gas is within the range from 6 to 2000 milliliters per minute.

36. A method as in claim 35 wherein the rate of flow of said stream of intermixed sample and carrier gases within said capillary gas chromatograph is sufficient to attain an optimum average linear flow velocity of the order of 13 to 25 centimeters per second within the capillary column of said gas chromatograph.

37. A method as in claim 35 wherein the rate of flow of such stream of carrier gas is above about 70 milliliters per minute.

38. A method as in claim 33 wherein the analysis sample introduced to the chromatograph column is of the order of 0.01 microliters.

39. In a linear fractionation method for providing substantially pure sample aliquots for capillary gas chromatography, the steps of preheating a stream of carrier gas, introducing said stream of carrier gas to an outer inert annular passage, reversing the direction of said stream of carrier gas to pass inwardly of said outer passage through an inner inert core passage, heating said outer and inner passages to maintain a desired elevated temperature of said carrier gas, introducing an analysis sample to said stream of carrier gas at the point of reversal of direction of said stream so as to flow with said stream of carrier gas through said core passage, said carrier gas serving to vaporize said sample and thereby form a mixed gaseous stream containing vaporized sample and carrier gas, introducing said mixed gaseous stream to an inert tortuous pathway wherein the direction of flow of said mixed gaseous stream is reversed a sufficient number of times to obtain a substantially complete turbulent mixing of said vaporized sample and carrier gases, and directing a predetermined volume of hot intermixed sample and carrier gases to the inlet of a capillary gas chromatograph to thereby cause separation of a desired aliquot of the same for capillary chromatographic analysis, the vaporization and intermixing of said sample and the separation of said desired aliquot of intermixed sample and carrier gases taking place wholly within the inert nonreactive environment of said annular and core passages and said tortuous pathway.

40. A method as in claim 39 wherein the inert nonreactive environment of said annular and core passages is maintained by the steps of periodically cleaning exposed surfaces of the same with solvent and thereafter subjecting said exposed surface to the action of a silylanizing reagent.

* * * * *